United States Patent [19]
Hsieh et al.

[11] Patent Number: 5,359,638
[45] Date of Patent: Oct. 25, 1994

[54] METHOD FOR RECURSIVE FILTERING RESIDUAL AFTERGLOW FROM PREVIOUS COMPUTED TOMOGRAPHY SCANS

[75] Inventors: Jiang Hsieh, Waukesha; Robert F. Senzig, Germantown, both of Wis.

[73] Assignee: General Electric Company, Milwaukee, Wis.

[21] Appl. No.: 860,659

[22] Filed: Mar. 30, 1992

[51] Int. Cl.$^5$ ........................................ G01N 23/083
[52] U.S. Cl. .................................... 378/4; 378/901; 250/252.1; 364/413.17
[58] Field of Search .................... 378/4, 901; 250/252.1 R; 364/413.21, 413.19, 413.17, 413.14

[56] References Cited

U.S. PATENT DOCUMENTS

| | | | |
|---|---|---|---|
| 4,112,303 | 9/1978 | Brandt | 250/445 T |
| 4,115,695 | 9/1978 | Kelman | 250/445 T |
| 4,233,662 | 11/1980 | LeMay | 364/414 |
| 4,494,141 | 1/1985 | Altekruse | 358/111 |
| 4,583,240 | 4/1986 | Gatten et al. | 378/19 |
| 4,707,607 | 11/1987 | Whetten | 250/385 |
| 5,249,123 | 9/1993 | Hsieh | 364/413.19 |
| 5,265,013 | 11/1993 | King et al. | 364/413.21 |

Primary Examiner—Paul M. Dzierzynski
Assistant Examiner—David V. Bruce
Attorney, Agent, or Firm—Quarles & Brady

[57] ABSTRACT

A computed tomography imaging system has a source of radiation and a radiation detector that has an exponential impulse response characterized by a plurality of N components with different time constants. The source and the detector are revolved about an object to be imaged and the output of the detector is sampled periodically to acquire a set of radiation attenuation values, with the values for each revolution being designated as a scan. A recursive filter function is applied sequentially to the radiation attenuation values from a given scan to generate approximated values for variables of the filter function that define residual detector response from the previous scan. A set of filtered attenuation values then is produced by applying the filter function again to the radiation attenuation values from the given scan. The approximated values for variables are used when the filter function is applied to the first radiation attenuation value of the scan. An image is reconstructed from the set of filtered attenuation values.

7 Claims, 5 Drawing Sheets

METHOD FOR RECURSIVE FILTERING RESIDUAL AFTERGLOW FROM PREVIOUS COMPUTED TOMOGRAPHY SCANS

The present invention relates to computed tomography imaging systems; and particularly to techniques which compensate for afterglow artifacts in output signals from X-ray detectors used in such systems.

BACKGROUND OF THE INVENTION

As shown in FIG. 1, a computed tomography (CT) scanner for producing images of the human anatomy includes a motorized patient table 10 which positions a patient at different depths within aperture 11 of a gantry 12. A source of collimated X-rays 13 is mounted within the gantry 12 to one side of its aperture 11, and an array of X-ray detectors 14 is mounted to the other side of the aperture. The X-ray source 13 and detectors 14 revolve about aperture 11 during a scan of the patient to obtain X-ray attenuation measurements from many different angles. U.S. Pat. Nos. 4,112,303 and 4,115,965 disclose the details of the gantry construction, and U.S. Pat. No. 4,707,607 describes the detector array 14. The descriptions of the components in these patents are incorporated herein by reference.

A complete scan of the patient is comprised of a set of X-ray attenuation measurements which are made at different angular orientations of the X-ray source 13 and detector 14 in one revolution about the patient. The gantry may stop or continue to move as the measurements are being made. An attenuation measurement at a given orientation is referred to in the art as a "view" and the set of measurements at a view forms a "transmission profile." As shown in FIG. 2, the X-ray source 13 produces a fan-shaped beam that passes through the patient and impinges on an array of detectors 14. Each detector 14 in this array produces a separate attenuation signal and the signals from all the detectors 14 are separately acquired to produce the transmission profile for the indicated angular orientation. The profiles are stored in a disc memory as raw, or uncompensated, data. The X-ray source 13 and detector array 14 continue to revolve in direction 15 to a another angular orientation where the next transmission profile is acquired.

The resultant transmission profiles from the scan then are used to reconstruct an image which reveals the anatomical structures in a slice taken through the patient. The prevailing method for reconstructing image is referred to in the art as the filtered backprojection technique. This process converts the attenuation measurements from a scan into integers called "CT numbers" or "Hounsfield units", which are used to control the brightness of a corresponding pixel on a cathode ray tube display.

Each X-ray detector 14 comprises a scintillator and a solid state photodiode. X-rays striking the scintillator produce light photons which are absorbed by the photodiode creating an electric current. The light is not emitted by the scintillators instantaneously, rather the emission follows a multi-exponential curve. Similarly, the light emission does not terminate immediately when the X-ray beam is extinguished, but produces a response from the detector having a decay which can be defined by a multi-exponential function. The time dependence of the output signal intensity can be modelled accurately as a sum of several different time constant decay components.

Because the detector array is rotating rapidly about the patient, the exponential decay blurs together detector readings for successive views creating an adverse effect that is referred to as "afterglow". The afterglow is a function of the intensity of the X-ray flux and the response characteristics of the detector, and degrades azimuthal resolution of the image and produces shading and arc shaped artifacts. The azimuthal direction 16 of the image area is transverse to a line 17 radiating from the center of the imaging aperture 11. The amount of blurring increases the farther the object is spaced from the aperture center, since the speed at which the object is swept across the detectors 14 effectively increases with this spacing.

FIG. 3 plots attenuation values from a given detector for a series of views and graphically depicts the blurring. The solid line represents the output of a single detector 14 during several views for a square object being imaged. Ideally the detector data should have a rectangular shape as represented by the dashed lines. However, the effect of the afterglow blurring rounds the edges of the waveform and extends the object signal into several adjacent views. When the views are used to reconstruct an image, the object will appear enlarged and will not have sharp, distinct edges.

The CT system may be operated in either the axial mode, the helical scan mode or the cine mode. In the axial mode, the table 10 is stationary during each scan and the gantry revolves once to complete a scan. A compensation technique for the afterglow artifacts in the axial mode has been proposed in U.S. Pat. No. 5,249,123 entitled "COMPENSATION OF COMPUTED TOMOGRAPHY DATA FOR DETECTOR AFTERGLOW ARTIFACTS". This method uses the detector output sample from the previous view to derive a compensation value for each detector response decay component. The sample for the present view is adjusted according to the compensation values to remove the afterglow artifacts. The compensation values for the first view of the scan are zeroes, since a relatively long time occurs between scans allowing the afterglow to decay to a negligible level.

In the helical scan mode, the gantry revolves through many revolutions and the table moves the patient through the aperture 11 during the examination. A helical scan is subdivided to a series of individual scans, each comprising one revolution of the gantry and the data acquired during each individual scan is stored in a separate file in the CT system. In the helical mode, time between each individual scan is equivalent to the time between each view within a scan and the afterglow no longer decays to a negligible level before the next scan starts. Therefore, the first view of each scan in the helical mode will be affected by the afterglow from the last view of the previous scan.

As the data for the helical scan is stored as separate files for each individual scan, attenuation data for the previous scan is not available for deriving compensation values for the afterglow in the next scan in the helix. Merely setting the compensation values for the first view in each scan to zero does not eliminate the afterglow artifacts. This problem also occurs in the cine mode in which the table remains stationary while the gantry moves continuously through many revolutions acquiring a series of individual scans. Therefore, another technique must be employed to compensate for afterglow in the first view of successive individual scans in the helical and cine scan modes.

Further, the image data are archived as raw, uncompensated, attenuation measurement values and a similar problem exists during subsequent reconstruction of an image from the archived data. A technician is able to specify any location in the helical scan data at which to begin image reconstruction and the reconstruction process uses one revolution worth of views from that point. Whenever a location other than the first acquired view is specified, the computer processor will lack information about the previous views from which to compute afterglow compensation values for the first view of the reconstruction.

SUMMARY OF THE INVENTION

A computed tomography imaging system includes a source of radiation and a detector array which produces an output signal representing the level radiation received from the source. Every detector has an exponentially decaying impulse response that can be modelled accurately as a sum of a plurality of N component functions with different time constants. The source and detector array are revolved around an object to be imaged and the signal from each detector is sampled every interval $\Delta t$ to produce a radiation attenuation value. The values acquired during each revolution are designated as a scan.

Conventional techniques are employed to reconstruct an image from the radiation attenuation value. However, before doing so, the values are processed to remove the effects of the non-ideal response of the detector. A point is specified in the set of radiation attenuation values at which the reconstruction process is to begin, thereby defining a group of radiation attenuation values to be used in reconstructing the image.

The following expression is applied to a plurality of attenuation values in the group:

$$x_k = \frac{y(k\Delta t) - \sum_{n=1}^{N} (\beta_n e^{-\Delta t/\tau_n}) S_{nk}}{\sum_{n=1}^{N} \beta_n}$$

where $y(k\Delta t)$ designates the radiation attenuation value acquired during the kth interval, $\beta_n = \alpha_n(1 - e^{-\Delta t/\tau_n})$ in which $\alpha_n$ represents the strength of an impulse response component n having time constant $\tau_n$, and $S_{nk} = X_{k-1} + e^{-\Delta t/\tau_n} S_{n(k-1)}$. This generates a value for each variable $S_{nk}$ from the last radiation attenuation value to which the expression was applied.

The expression is applied sequentially again to each radiation attenuation value in the group to produce a plurality of filtered values $x_k$. When applying the above expression to the first radiation attenuation value in the group at least one of the values for variables $S_{nk}$ are used in the expression. In the preferred embodiment of the present invention, zero values are used for variables $S_{1k}$ and $S_{2k}$ which correspond to the components having the shortest time constants and the values for the remaining variables $S_{nk}$ obtained from the previous application of the expression are used with the first radiation attenuation value. An image is reconstructed from the filtered values.

An object of the present invention is to provide a technique which alters the X-ray attenuation measurements from each detector to remove the effects produced by a non-ideal radiation response of the detector.

Another object is to provide a filtering operation that compensates for the different components of the multiple exponential response of the radiation detector.

DESCRIPTION OF THE PRESENT INVENTION

Figure 1:
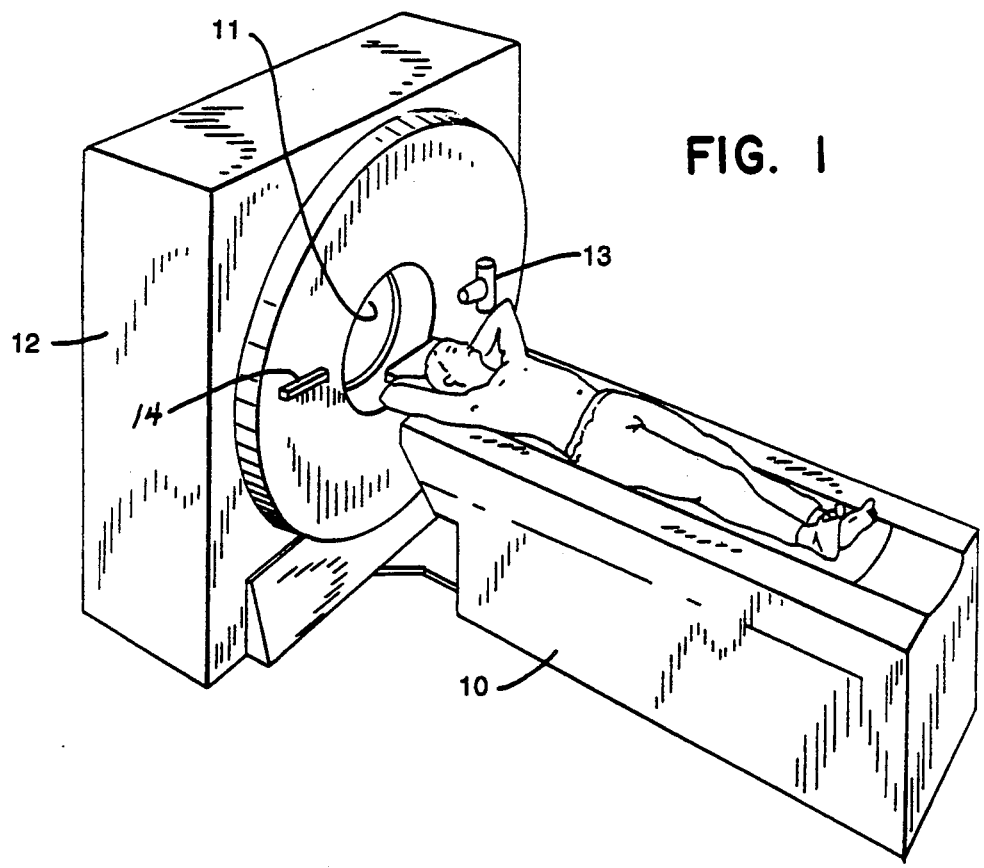
FIG. 1 is a perspective view of a CT imaging system in which the present invention may be employed.
Figure 2:
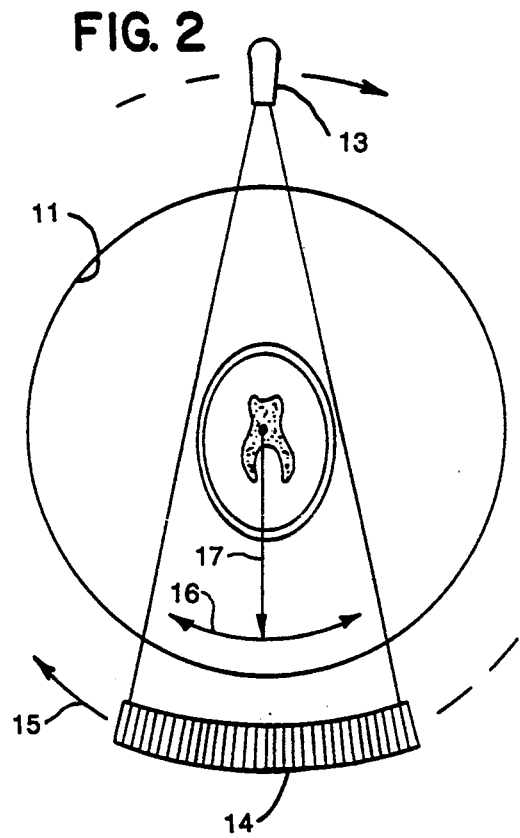
FIG. 2 is a schematic representation of a scanning technique employed in the CT imaging system.
Figure 3:
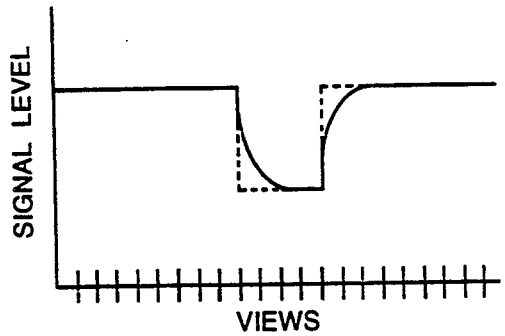
FIG. 3 is a graph illustrating the response of an ideal detector and an actual detector which has resolution degradation due to afterglow.
Figure 4:
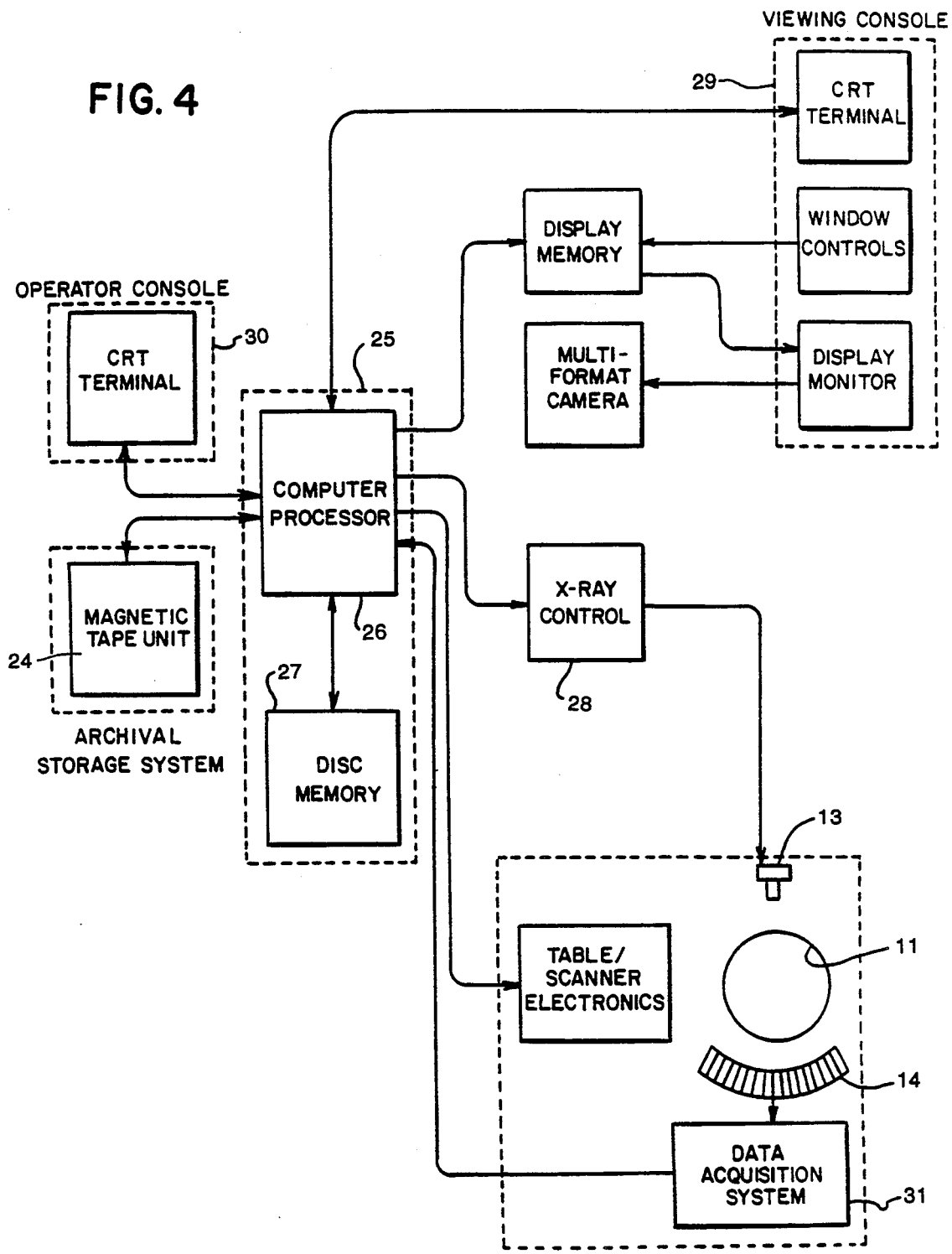
FIG. 4 is a block diagram of the signal processing circuitry in the CT imaging system.
Figure 5:
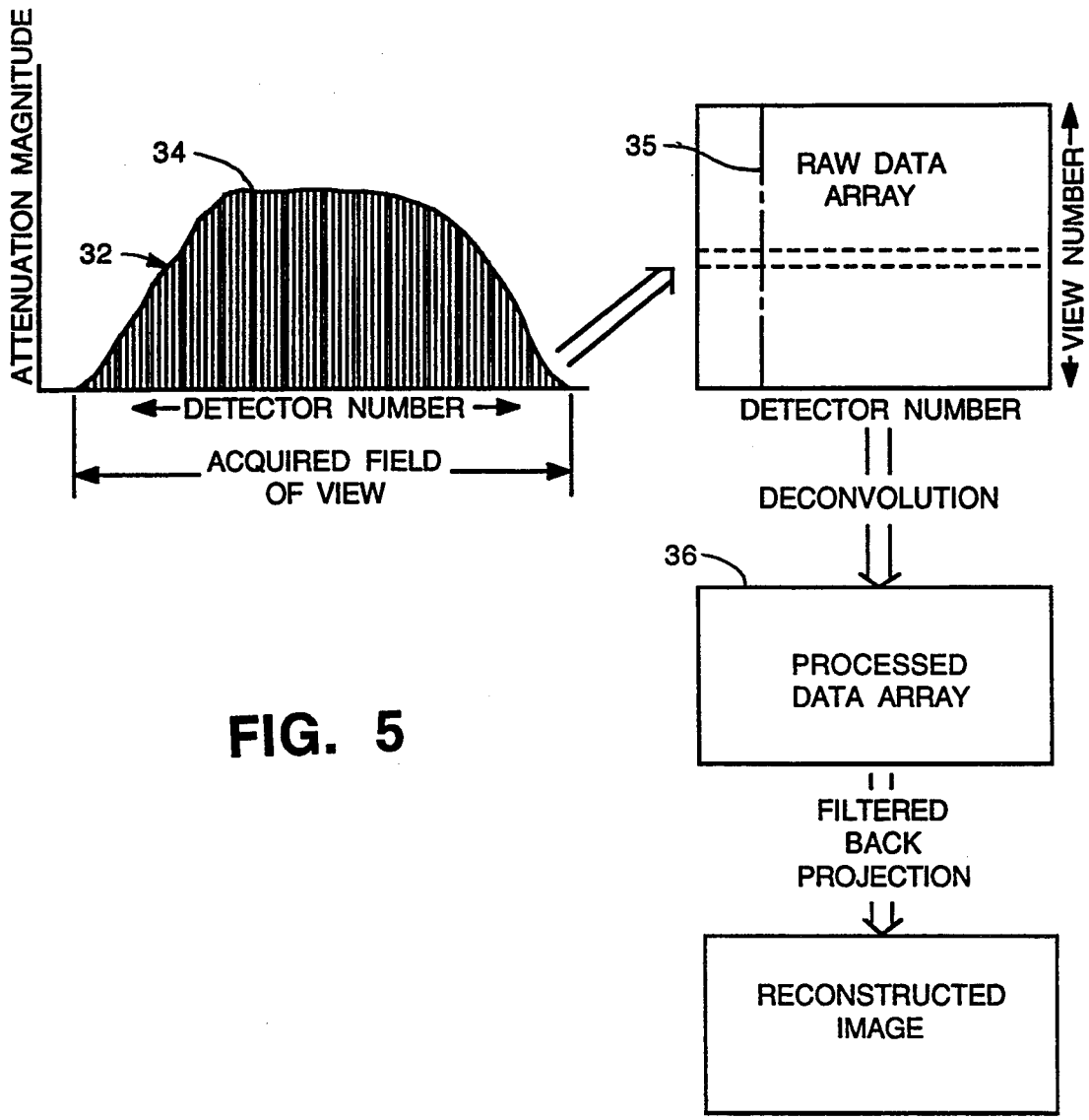
FIG. 5 is a graphical representation of data which is acquired and processed by the CT imaging system.

With reference to FIGS. 1, 2 and 4, the operation of the CT imaging system is controlled by a programmable data processing system 25 which includes a computer processor 26 and a disc memory 27. The disc memory 27 stores the programs that the computer processor 26 uses in patient scanning and in image reconstruction and display. It also stores, on a short-term basis, the acquired data and the reconstructed image data. The computer processor 26 includes a general purpose minicomputer with input and output ports suitable for connection to the other system components as shown and an array processor, such as that disclosed in U.S. Pat. No. 4,494,141. The description of the array processor in that patent is incorporated herein by reference.

An output port on the computer processor 26 connects to a conventional X-ray control circuit 28, which in turn controls excitation of the X-ray source 13. The high voltage on the X-ray source 13 is controlled and its cathode current is regulated to provide the correct dosage. The high voltage and cathode current are selected by an X-ray technician via an operator console 30 and the computer processor 26 directs the production of the X-rays in accordance with its scan program.

The X-rays disperse in a fan-shape and are received by the array of detectors 14 mounted on the opposite side of the gantry aperture 11. Each individual detector examines a single ray originating from the X-ray source 13 and traversing a straight line path through a patient located in the aperture 11. The currents formed in each detector 14 are collected as an analog electrical signal which is a measurement of the X-ray attenuation as the beam passes through the patient. The signal from each detector is converted into a digital X-ray attenuation values by analog-to-digital converters in a data acquisition system 31, such as the one disclosed in in U.S. Pat. No. 4,583,240 which is incorporated herein by reference.

The digital attenuation values from the data acquisition system 31 are preprocessed by the computer processor 26 in a well known manner to compensate for "dark currents", uneven detector sensitivities and gains, and variation of the X-ray beam intensity throughout the scan. This is followed by beam hardening corrections and conversion of the data to logarithmic form so that each measured value represents a line integral of the X-ray beam attenuation. The attenuation values 32 in each view are stored as one row of a two-dimensional raw data array 33 in the disc memory 27. The raw radiation attenuation values are archived in magnetic tape unit 24 enabling an image to be reconstructed from the data at a much later point in time.

Each row of attenuation data provides a transmission profile of the object to be imaged when viewed from a single angle. Each column 35 of data in the array represents the data acquired from a given detector during a scan. Therefore, one dimension of this array is determined by the number of views, or attenuation values, which are acquired during the scan and the other dimension is determined by the number of detectors sampled during each view. For example, signals from up to 852 detectors may be sampled approximately 1000 times during a scan to produce an equivalent number of views. In the helical scan mode a separate array of data for each scan, or revolution of the gantry, are stored in the disc memory during each examination of the patient.

The raw attenuation data stored in the array have been corrupted by the afterglow artifacts due to the response time lag of each detector. If the raw data are used to reconstruct an image, features of the image will be blurred and artifacts will be present as described previously. However, the present system provides a mechanism which compensates for resolution degradation, shading and arc artifacts due to these effects. In order to define the compensation, or filtering mechanism, the response of the type of detector used in the array has to be characterized.

The impulse response of each detector in the array can be modelled by the equation:

$$h(t) = \sum_{n=1}^{N} \frac{a_n}{\tau_n} e^{-t/\tau_n} \quad (1)$$

where n designates one of N components of the exponential response which component has a relative strength $a_n$ and a time constant $\tau_n$. The response of one type of detector has been characterized accurately by four (N=4) decay components having time constants of 1, 6, 40 and 300 milliseconds.

In order to determine a correction mechanism for the image artifacts, one must understand the afterglow effect. The detector response y(t) to input signal x(t) can be expressed as the convolution of the detector impulse response h(t) and the input signal x(t):

$$y(t) = h(t) * x(t) \quad (2)$$

$$y(t) = \int_{-\infty}^{t} x(t') \sum_{n=1}^{N} \frac{a_n}{\tau_n} e^{-(t-t')/\tau_n} dt'$$

Equation (2) can be simplified because the input signal x(t) is a causal function, allowing the summation and integration to be interchanged in the equation. Furthermore the integration region [0,t] can be divided into k intervals corresponding to the period between views with each interval being denoted by $\Delta t$ ($k\Delta t = t$). when these factors are considered, the actual attenuation value $x_k$ for the kth view can be expressed for relatively small values of $\Delta t$ by the equation:

$$x_k = \frac{y(k\Delta t) - \sum_{n=1}^{N} a_n (1 - e^{-\Delta t/\tau_n}) \sum_{j=1}^{k-1} x_j e^{-(k-j)\Delta t/\tau_n}}{\sum_{n=1}^{N} a_n (1 - e^{-\Delta t/\tau_n})} \quad (3)$$

where $y(k\Delta t)$ is the raw attenuation value from the detector acquired during the kth view. Although this equation expresses the relationship between the sample of the detector signal and the actual radiation level that produced that sample, it can not be implemented easily as the calculation for a given value requires values for the detector samples from all the previous views in current scan.

To overcome that difficulty equation (3) can be rewritten into the form:

$$x_k = \frac{y(k\Delta t) - \sum_{n=1}^{N} \beta_n e^{-\Delta t/\tau_n} [x_{k-1} + e^{-\Delta t/\tau_n} [x_{k-2} + \ldots + e^{-\Delta t/\tau_n} (x_2 + e^{-\Delta t/\tau_n} x_1) \ldots ]]}{\sum_{n=1}^{N} \beta_n}$$

where $\beta_n = a_n (1 - e^{-\Delta t/\tau_n})$. If the contents enclosed by the outermost brackets in the immediately preceding equation are denoted as $S_{nk}$, the following relationship exists:

$$x_k = \frac{y(k\Delta t) - \sum_{n=1}^{N} [\beta_n e^{-\Delta t/\tau_n}] S_{nk}}{\sum_{n=1}^{N} \beta_n} \quad (5)$$

where the denominator and the bracketed portion of the numerator are constants. The terms $S_{nk}$ for the present attenuation value are functions of similar terms $S_{n(k-1)}$ for the attenuation value from the previous view, as given by $S_{nk} = x_{k-1} + e^{-\Delta t/\tau_n} S_{n(K-1)}$, in which $x_{k-1}$ is the actual attenuation value derived from the detector signal sample from the previous view. Zero values are used for $S_{nO}$ for the first view of each helical scanning process. Thus to derive the actual attenuation value from a given detector signal sample, only that detector sample and data from the processing of the immediately preceding sample need to be known. As a result, equation (5) can be implemented as a recursive filter by the array processor in computer processor 26. A special case exists for the first view of each subsequent scan of the helical scanning process, as will be described.

Figure 6:
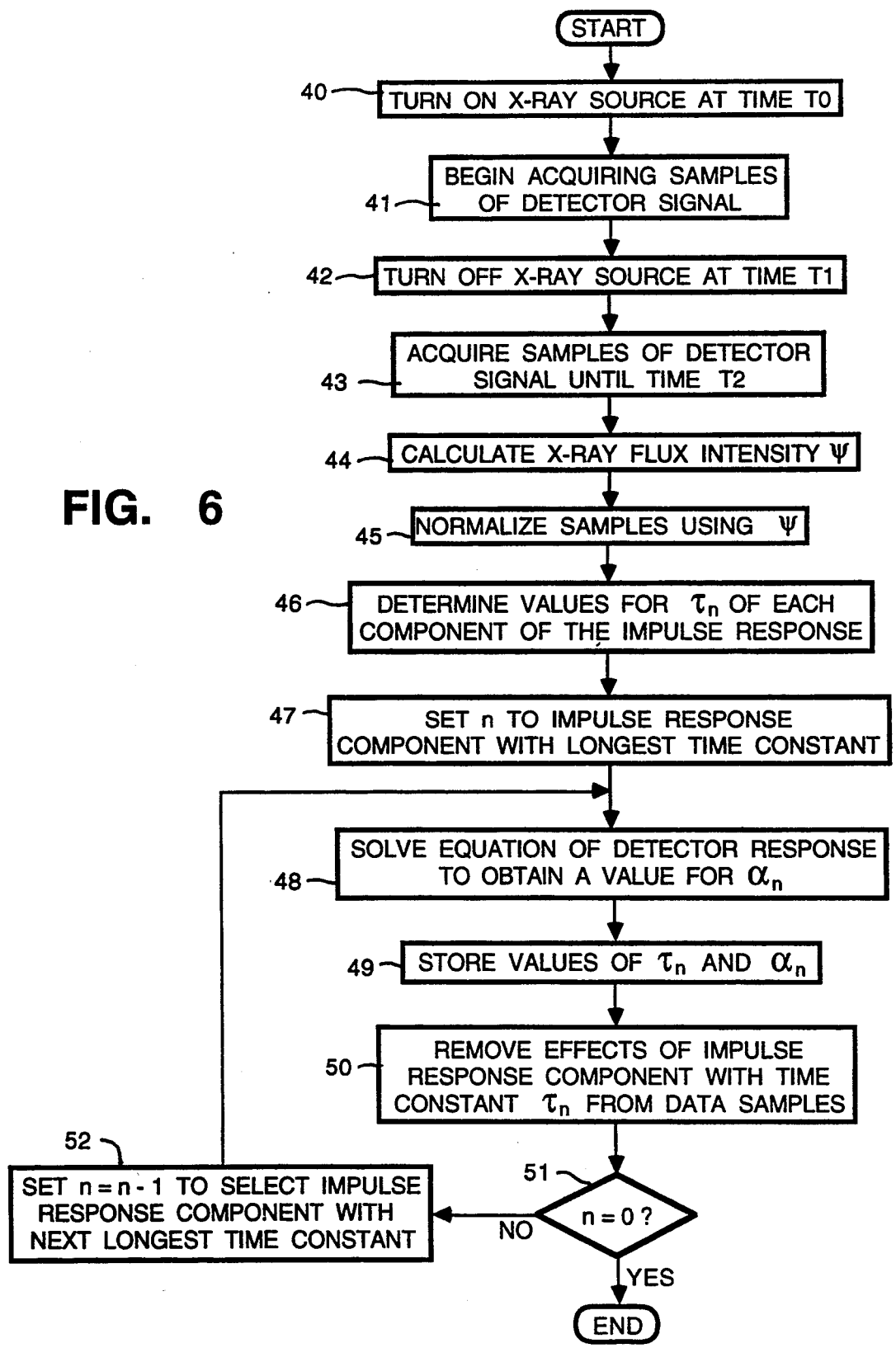
FIG. 6 is a flowchart of the process by which a given X-ray detector is characterized for the present compensation technique.

In order to apply the filter function in equation (5) to real image data, the response for each detector in the array 14 must be characterized by deriving values for $a_n$ and $\beta_n$ for each time constant component of every detector. This is accomplished in the factory by operating the CT system without an object present in the imaging aperture 11. With reference to FIG. 6, he X-ray source 13 turned on at time $t_0$ for a period of mime that is sufficiently long so that the detector response can reach its full magnitude, e.g. approximately half of the normal scan mime (step 40). Digital samples of the signal from each detector begin to be acquired at step 41. Then at step 42, the X-ray beam then is turned off at time $t_1$.

Continuing through step 43, the output signal from each detector in array 14 is sampled individually while the X-ray beam is active and for one second thereafter, for example. The samples of the detector signals are stored in an array similar to the one used for the attenuation values during imaging.

The detector response during the characterization process is defined by the expressions:

$$y(t) = \Psi \quad \text{for } t_0 < t < t_1, \text{ and} \tag{6}$$

$$y(t) = \Psi \sum_{n=1}^{N} a_n e^{(t-t_1)/\tau_n} \quad \text{for } t \geq t_1.$$

The digital samples of the detector output signal acquired while the X-ray beam is on ($t_0 < t < t_1$) are averaged at step 44 and the result is used to derive a value for the X-ray flux intensity $\Psi$. The samples acquired after the termination of the X-ray beam is divided by the value of $\Psi$ to normalize the data and the logarithm of the normalized data then is taken at step 45.

Then values for $\alpha_n$ and $\beta_n$ of each time constant component of the exponential response are determined next. As noted previously, the impulse response of one type of detector has been characterized accurately by four decay components having time constants $\tau_n$ of 1, 6, 40 and about 300 milliseconds, although the exact time constants may vary for other detectors. These time constants were determined graphically by plotting the detector signal samples representing the decay for a number of detectors of the same type and averaging the resultant time constants at step 46. The set of time constants then are used in determining a value of the relative strength $\alpha_n$ of the corresponding impulse response component of other detectors. Although using a common set of time constants appears to be satisfactory in determining values for $\alpha_n$, a set of time constants can be derived individually for each detector being characterized.

The values of $\alpha_n$ for a given detector are found in descending order starting with the response component having the longest time constant (e.g. n=4) at step 47. A detector signal sample is selected that was acquired at time T e.g. 300 msec.) after the X-ray beam extinguished at which time the effects of all except the longest time constant component are negligible. By using the logarithmic values of the detector samples, equation (6) can be simplified to $\log[y(T)] = \log \alpha_n - (T/\tau_n)$. The simplified equation is solved for $\alpha_4$ of the fourth (n=4) time constant component at step 48. Then at step 49 the estimated values for $\alpha_4$ and $\tau_4$ are stored in the computer processor memory.

Using the estimated values for $\alpha_4$ and $\tau_4$, the contribution of the longest time constant component to the measured decaying signal data can be calculated and removed from that data at step 50. The process (steps 48-52) is repeated for the next longest time constant component of the detector response, and so on for each of the remaining components. When all of the values of $\alpha_n$ and $\tau_n$ for a given detector have been estimated, n will equal zero at step 51 and the process will terminate. This characterization process is performed for each of the detectors 14 in the array.

Then the values of $\alpha_n$ and $\tau_n$ are employed to derive the constant terms of equation (5) for each of the four time constant components of every detector's response. These constants are stored in tables in the disc memory 27 for later used in filtering real image data.

Another table is established in the memory of the computer processor to store values of variables $S_{nk}$ (e.g. $S_{1k}$, $S_{2k}$, $S_{3k}$, and $S_{4k}$) for each detector in the array. At the beginning of a helical scanning process, the entries in this latter table are set to an initial value of zero (e.g. $S_{n0}=0$). As each new filtered attenuation value is determined, new values for $S_{nk}$ are calculated and stored in the table.

During the first scan of the helix, the array processor of the computer processor 26 applies the filter function defined by equation (5) to the raw X-ray attenuation values. Depending upon the speed of the array processor, the recursive filter function either can be applied in real-time as each detector sample is received from the data acquisition system 31 or, as currently is the case, the raw X-ray attenuation values are stored in the disc memory 27 and filtered later.

For simplification, the filtering process will be described in respect of data from one detector, with it being understood that the process is performed in parallel for each detector 14 in the array. Equation (5) is applied to each raw X-ray attenuation value $y(k\Delta t)$ from the detector to remove the effects due to the non-ideal response of the detector and calculate the actual, or filtered, value $x_k$ of the attenuation measurement. The filtered attenuation value is stored in another array in the disc memory 27. Separate constant terms and values for $S_{nk}$ are used for the samples from each detector. The values of $S_{n0}$ are zero for the first sample from each detector during a given helical scanning of the patient. Thereafter, new values for $S_{nk}$ are calculated for each detector every time another filtered attenuation value $x_k$ is derived for a given scan.

A back projection technique is employed to reconstruct an image from the filtered data for the first scan of the helix. The newly formed image is displayed on a monitor in the operator console 30.

However, when data for another scan within a helix is to be processed, the storage of data from each scan in a separate file does not allow the computer processor 26 access to data from the previous scan. This precludes being able to calculate values for $S_{nk}$ from the previous attenuation values. Thus for the first view of subsequent individual scans in the helical scan or for the first view when image reconstruction begins in the middle of a helical scan, a different compensation process is used. This process involves two processing passes through the scan data.

Figure 7:
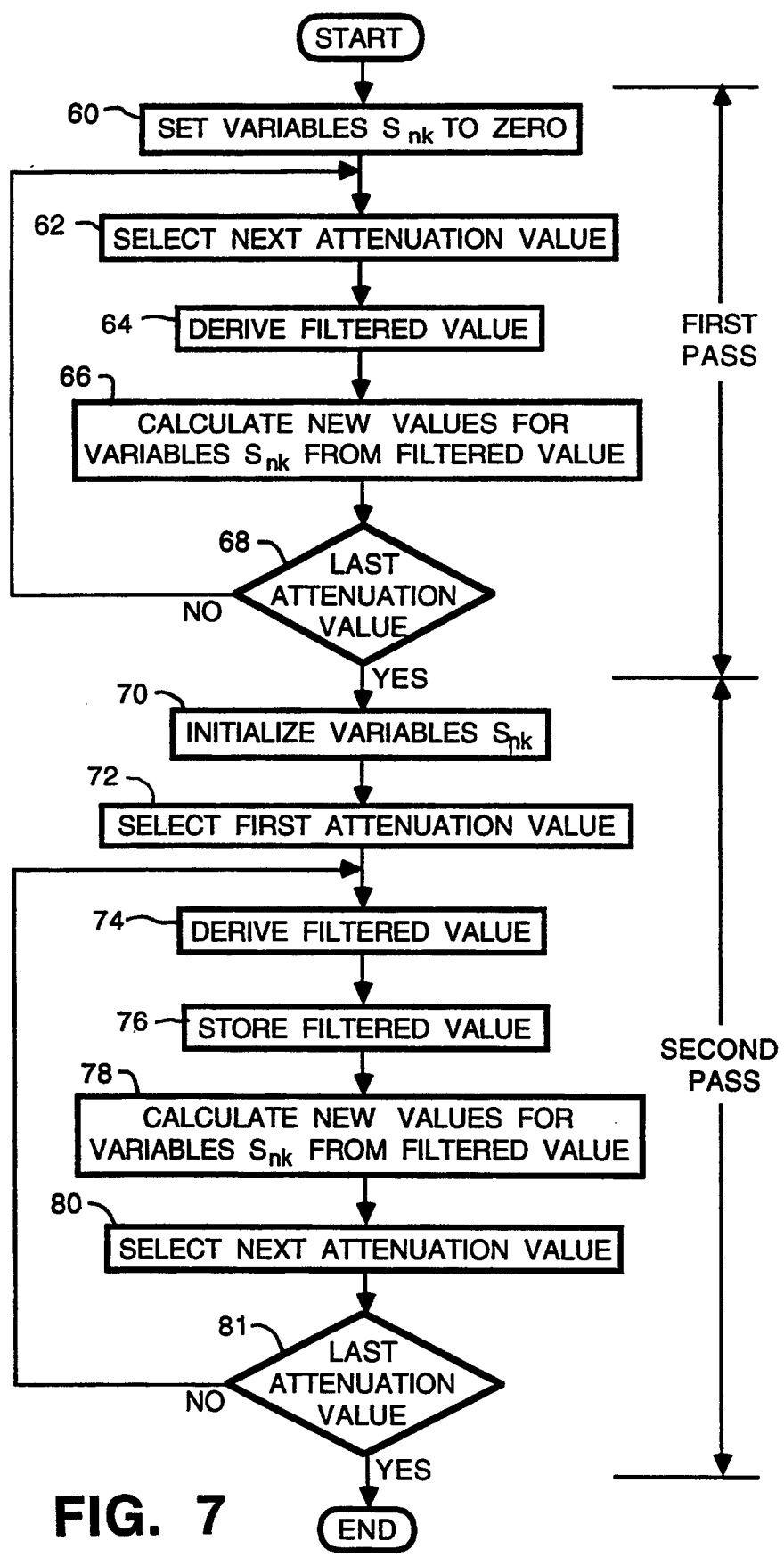
FIG. 7 is a flowchart of the compensation process for the first view in a scan.

The first pass is performed to calculate a set of $S_{nk}$ values for the last attenuation value in the scan sequence that will be used in image reconstruction. The calculation is performed in a similar manner as was used for the first scan of the helix, except that filtered values are not stored in an array. Specifically as shown in FIG. 7, the values for $S_{n0}$ initially are set to zero at step 60. At step 62 the first attenuation value is selected and equation (5) is solved for a filtered value at step 64.

The filtered value is used to calculate a new set of values for variables $S_{nk}$ at step 66. The program execution loops through steps 62-68 until all of the attenuation values in the scan have been processed at which time the program advances to step 70. At the end of the first processing pass, a resultant set of values for the four $S_{nk}$ variables for the last view of the scan are stored in the computer processor memory.

As the table on which the patient lies does not advance significantly during a single rotation of the gantry, the afterglow from the last views in consecutive scans are similar. This means that the resultant set of $S_{nk}$ values from the first pass is a close approximation of $S_{nk}$ values for the final view in the previous scan. Thus the resultant set of $S_{nk}$ values can be used to derive a filtered value from the first radiation attenuation value in the present scan. However, if all of the resultant values are used, linear streaks appear in the reconstructed image. It has been determined that the components with the shortest time constants contribute more significantly than other components to the afterglow artifacts. As a result, relatively small errors in the approximation of $S_{nk}$ for the shorter time constant components have a perceptible affect in the reconstructed image.

To avoid the streaking, only the $S_{nk}$ values for the longer time constant decay components are used to derive a filtered attenuation value for the first view in the non-initial helix scans and the $S_{nk}$ values for the shorter time constant decay components are set to zero at step 70. For a CT detector impulse response characterized by four time constants $\tau_n$ of 1, 6, 40 and about 300 milliseconds, the $S_{nk}$ values for the first two decay components ($S_{10}$ and $S_{20}$) are set to zero. The $S_{nk}$ values for the remaining decay components ($S_{30}$ and $S_{40}$) are set to the corresponding resultant values from the raw attenuation value of the last view processed by the first pass. At step 74, the first attenuation value of the scan is selected and program execution advances to step 74 for the second pass.

The filtered values are derived during a second processing pass through the raw attenuation values with the selected values for $S_{nk}$ used to process data from the first view of the scan. Each raw X-ray attenuation value $y(k\Delta t)$ in the present scan then is used in equation (5) to filter out the effects due to the non-ideal response of the detector and calculate the actual, or filtered, value $x_k$ of the attenuation measurement. The second pass comprising steps 74–81 utilizes same general process is used in the first pass. Specifically, separate constant terms and values for $S_{nk}$ are used for the samples from each detector with new values for $S_{nk}$ is calculated every time another filtered attenuation value $x_k$ is derived. However, each filtered attenuation value now is stored as an array in the disc memory 27 at step 76. After looping through steps 74–81 to process each attenuation value in the scan, the program terminates. An image then is reconstructed from the array of filtered values and is displayed on a monitor in the operator console 30.

Several variations of the present afterglow compensation technique can be used in order to reduce the processing time. In one case, the time required for the first pass can be decreased by not processing all of the views in the selected scan. For example, if an individual scan of the helix has 984 views and is performed in one second, each view takes about one millisecond. Therefore, using only the last 584 views can provide reasonably accurate approximations of the $S_{nk}$ values of the last view in the previous scan, as the earlier views in the present scan will have minimal contribution to the afterglow from the last view. Although using fewer views will further decrease the time required for the first pass, artifacts will begin to appear in the reconstructed image as fewer and fewer views are used.

In another variation to decrease the processing time, the number of views used in the first pass can be reduced by summing raw attenuation values for several views together and considering the sum as a single view when calculating values for $S_{nk}$. It should be understood the value of at used in the equations increases in proportion to the number of views being summed. For a scan having 984 views satisfactory results were achieved be summing adjacent groups of 4, 8, 24 and 41 views, although other sized groups can be used as well. In this case, the views are not summed during the second processing pass.

The invention being claimed is:

1. A method for producing an image in a computed tomography system, having a source of radiation and a detector for sensing radiation from said source and producing an output signal representing the sensed radiation, said detector having an exponential impulse response that is characterized by N components having different time constants, where N is a positive plural integer; the method comprising the steps of:

rotating said source of radiation and said detector about an object to be imaged;

periodically sampling the output signal from said detector at an interval $\Delta t$ to acquire a set of radiation attenuation values;

sequentially applying the following expression to a plurality of radiation attenuation values:

$$x_k = \frac{y(k\Delta t) - \sum_{n=1}^{N} (\beta_n e^{-\Delta t/\tau_n}) S_{nk}}{\sum_{n=1}^{N} \beta_n}$$

where $y(k\Delta t)$ designates the radiation attenuation value acquired during the kth interval, $\beta_n = \alpha_n(1 - e^{-\Delta t/\tau_n})$ in which $\alpha_n$ represents the strength of an impulse response component n having time constant $\tau_n$, and $S_{nk} = X_{k-1} + e^{-\Delta t/\tau_n} S_{n(k-1)}$, to generate a set of values for variables $S_{nk}$;

producing a plurality of filtered values $X_k$ by applying the above expression to each radiation attenuation value, wherein values in the set of values for variables $S_{nk}$ are used in the expression applied to the radiation attenuation value which was acquired first; and reconstructing an image from the filtered values.

2. The method as recited in claim 1 wherein values of substantially zero are used for $S_{1k}$ and $S_{2k}$ which correspond to the components with the mime constants of shortest duration, and values in the set of values are used for other variables $S_{nk}$ in the expression applied to a first radiation attenuation value in the group.

3. The method as recited in claim 1 wherein values in the set of values for variables $S_{nk}$ which correspond to components having time constants that are less than seven milliseconds are not used in the expression applied to a first radiation attenuation value in the group.

4. A method for producing an image in a computed tomography system, having a source of radiation and a detector for sensing radiation from said source and producing an output signal representing the sensed radiation, said detector having an exponential impulse response that is characterized by N components having different time constants, where N is a positive plural integer; the method comprising the steps of:

energizing the source of radiation;

moving the energized source of radiation and the detector in a plurality of revolutions about an object to be imaged, each revolution being designated as a scan;

periodically sampling the output signal from the moving detector at an interval $\Delta t$ to acquire a set of radiation attenuation values during each scan;

sequentially applying the following expression:

$$x_k = \frac{y(k\Delta t) - \sum_{n=1}^{N} (\beta_n e^{-\Delta t/\tau_n}) S_{nk}}{\sum_{n=1}^{N} \beta_n}$$

where $y(k\Delta t)$ designates the radiation attenuation value acquired during the kth interval during the scan, $\beta_n = \alpha_n(1 - e^{-\Delta t/\tau_n})$ in which $\alpha_n$ represents the strength of an impulse response component n having time constant $\tau_n$, and $S_{nk} = X_{k-1} + e^{-\Delta t/\tau_n} S_{n(k-1)}$, to a plurality of radiation attenuation values acquired during a given scan to generate a set of values for $S_{nk}$;

producing a plurality of filtered values $X_k$ by sequentially applying the above expression to each radiation attenuation value for the given scan, wherein values in the set of values for $S_{nk}$ are used in the expression applied to the radiation attenuation value which was acquired first during the given scan; and reconstructing an image from the plurality of filtered values.

5. The method as recited in claim 4 wherein values of substantially zero are used for $S_{1k}$ and $S_{2k}$ which correspond to the components with the time constants of shortest duration, and values in the set of values are used for other variables $S_{nk}$ in the expression applied to the radiation attenuation value which was acquired first during the given scan.

6. The method as recited in claim 4 further comprising characterizing the response of the detector to derive values of $\alpha_n$ and $\tau_n$ by:

generating a beam of radiation from time $t_0$ to time $t_1$;

periodically sampling a signal produced by the radiation detector, such sampling occurs while the beam of radiation is being generated and continues until time $t_2$ which is later than time $t_1$, to produce a plurality of signal samples;

determining a time constant $\tau_n$ for each component of the impulse response from the plurality of signal samples;

calculating an X-ray flux intensity value $\Psi$ from a sample acquired between times $t_0$ and $t_1$; and deriving a value for $\alpha_n$ for each component of the impulse response from signal samples acquired between times $t_1$ and $t_2$ according to the expression:

$$y(t) = \Psi \sum_{n=1}^{N} \alpha_n e^{(t-t1)/\tau_n}.$$

7. The method as recited in claim 6 in which the step of deriving $\alpha_n$ comprises:

(a) using the calculated X-ray flux intensity value to normalize signal samples acquired between times $t_1$ and $t_2$ and then taking the logarithm of the normalized signal samples;

(b) selecting a normalized signal sample that was acquired at a time T at which all the components of the impulse response can be neglected except the component which has the longest time constant $\tau_n$;

(c) solving the expression $\log[y(T)] = \log \alpha_n - (T/\tau_n)$ for $\alpha_n$;

(d) removing the effects of the component of the impulse response which has the longest time constant $\tau_n$ from the signal samples;

(e) successively repeating steps (b) through (d) for each remaining components of the impulse response in descending order of time constant length, each time step (d) is executed the effects of the remaining component with longest time constant $\tau_n$ are removed from normalized signal samples.

* * * * *

UNITED STATES PATENT AND TRADEMARK OFFICE
CERTIFICATE OF CORRECTION

PATENT NO. : 5,359,638
DATED : October 25, 1994
INVENTOR(S) : Jiang Hsieh, et al.

It is certified that error appears in the above-indentified patent and that said Letters Patent is hereby corrected as shown below:

In column 6, at line 55, change $\beta_n$ to --$\tau_n$--.

In column 6, at line 59, change "mime" to --time--.

In column 6, at line 62, change "mime" to --time--.

In column 9, at line 66, change "at" to --$\Delta t$--.

In column 10, at line 29, delete the "(" at the very end of the line.

In column 10, line 30, add "(" before --1--.
In column 10, at line 43 (claim 2), change "mime" to --time--.

UNITED STATES PATENT AND TRADEMARK OFFICE
CERTIFICATE OF CORRECTION

PATENT NO. : 5,359,638
DATED : October 25, 1994
INVENTOR(S) : Jiang Hsieh, et al.

It is certified that error appears in the above-indentified patent and that said Letters Patent is hereby corrected as shown below:

Column 6, line 58, "he" should read --the--.

Signed and Sealed this

Twenty-fourth Day of January, 1995

Attest:

BRUCE LEHMAN

Attesting Officer

Commissioner of Patents and Trademarks